(12) United States Patent
Lane et al.

(10) Patent No.: US 9,517,012 B2
(45) Date of Patent: Dec. 13, 2016

(54) CONTINUOUS PATIENT MONITORING

(71) Applicant: Welch Allyn, Inc., Skaneateles Falls, NY (US)

(72) Inventors: John A. Lane, Weedsport, NY (US); Vuong B. Nguyen, Liverpool, NY (US); Kristin Ann Alisanski, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 118 days.

(21) Appl. No.: 14/026,802

(22) Filed: Sep. 13, 2013

(65) Prior Publication Data

US 2015/0077268 A1 Mar. 19, 2015

(51) Int. Cl.
*A61B 5/00* (2006.01)
*G08C 17/02* (2006.01)
*A61B 5/0205* (2006.01)
*G06F 19/00* (2011.01)

(52) U.S. Cl.
CPC ......... *A61B 5/0024* (2013.01); *A61B 5/02055* (2013.01); *A61B 5/746* (2013.01); *G06F 19/3406* (2013.01); *G08C 17/02* (2013.01); *A61B 5/0022* (2013.01)

(58) Field of Classification Search
USPC .................................................... 340/870.09
See application file for complete search history.

(56) References Cited

U.S. PATENT DOCUMENTS 5,517,988 A * 5/1996 Gerhard ............. A61B 5/14551
356/41
5,957,861 A 9/1999 Combs et al.
7,666,151 B2 2/2010 Sullivan et al.
8,370,080 B2 2/2013 Watson et al.
2005/0033188 A1* 2/2005 Whitaker ........... A61B 5/02233
600/490
2007/0118054 A1* 5/2007 Pinhas ................. A61B 5/1102
600/587

(Continued)

FOREIGN PATENT DOCUMENTS

WO 2009031149 A2 3/2009

OTHER PUBLICATIONS

Amir et al.; "An Automated Sleep-Analysis System Operated through a Standard Hospital Monitor"—Journal of Clinical Sleep Medicine, Feb. 15, 2010; 6(1): 59-63, American Academy of Sleep Medicine, PMCID: PMC2823277, 7 pages.

(Continued)

*Primary Examiner* — Firmin Backer
*Assistant Examiner* — Jerold Murphy
(74) *Attorney, Agent, or Firm* — Merchant & Gould P.C.

(57) ABSTRACT

A system for providing continuous monitoring of a patient includes: a first monitor device configured to measure one or more physiological attributes associated with the patient, the first monitor device being a contactless device; and a second monitor device configured to measure one or more physiological attributes associated with the patient, the second monitor device including one or more sensors contacting the patient; wherein, upon an alarm condition by the first monitor device, the second monitor device is configured to measure a physiological attribute and suppress the alarm condition when the second monitor device detects a non-alarm condition.

16 Claims, 4 Drawing Sheets

(56) References Cited

U.S. PATENT DOCUMENTS

| | | | |
|---|---|---|---|
| 2009/0040044 A1* | 2/2009 | Chiao | A61B 5/0002 340/540 |
| 2009/0069645 A1 | 3/2009 | Nielsen et al. | |
| 2009/0143655 A1 | 6/2009 | Shani | |
| 2010/0292544 A1 | 11/2010 | Sherman et al. | |
| 2010/0298659 A1 | 11/2010 | McCombie et al. | |
| 2012/0320079 A1* | 12/2012 | Feddes | G06T 11/206 345/593 |
| 2012/0323086 A1 | 12/2012 | Hansen | |

OTHER PUBLICATIONS

Yilmaz et al.; "Detecting Vital Signs with Wearable Wireless Sensors"—Sensors (Basel, Switzerland)—Multidisciplinary Digital Publishing Institute (MDPI) published online Dec. 2, 2010, PMCID: PMC3231103, 20 pages.

Palace et al.; "The Effect of a Continuous Patient Monitoring System on Reducing Falls and Hospitalization in Skilled Nursing Facilities"—The HebrewHome™ Riverdale, Bronx, NY, Dorot Geriatric Center, Netanya, Israel, EarlySense, accessed Sep. 13, 2013, 1 page.

EarlySense® Bedside Monitoring and Centralized Unit Patient Management System—MK65 Rev.4, EarlySense Proactive Patient Care, copyright EarlySense, accessed Sep. 13, 2013, 4 pages.

EarlySense® System Layout and Components—MK921 Rev. 1, EarlySense Proactive Patient Care, copyright EarlySense, accessed Sep. 13, 2013, 2 pages.

Terrance et al.; "Contact-Free Under-the-Mattress Monitoring for Early Recognition of and Response to Clinical Deterioration in Medical/Surgical Units"—California Hospital Medical Center, Los Angeles, CA, EarlySense®, accessed Sep. 13, 2013, 1 page.

Terrance et al.; "Contact-Free Under-the-Mattress Monitoring for Early Recognition of End-of-Life in Med/Surg Units"—California Hospital Medical Center, Los Angeles, CA, EarlySense LTD, Ramat Gan, Israel, EarlySense®, accessed Sep. 13, 2013, 1 page.

* cited by examiner

CONTINUOUS PATIENT MONITORING

BACKGROUND

The continuous monitoring of patients can be labor-intensive and time consuming. This is particularly true of patients that are recovering from surgery. The costs associated with caregivers monitoring the vital signs of post-surgical patients can be significant. This limits the number of patients that can be monitored by each caregiver and increases the medical costs. Automated systems that are used to provide such monitoring are sometimes inaccurate. Such systems can be plagued with inadequate monitoring and false alarming.

SUMMARY

In one aspect, a system for providing continuous monitoring of a patient includes: a first monitor device configured to measure one or more physiological attributes associated with the patient, the first monitor device being a contactless device; and a second monitor device configured to measure one or more physiological attributes associated with the patient, the second monitor device including one or more sensors contacting the patient; wherein, upon an alarm condition by the first monitor device, the second monitor device is configured to measure a physiological attribute and suppress the alarm condition when the second monitor device detects a non-alarm condition.

In another aspect, a system for providing continuous monitoring of a patient includes: a first monitor device configured to measure one or more physiological attributes associated with the patient, the first monitor device being a piezoelectric device that measures the physiological attributes without contact, and wherein the physiological attributes including heart rate, respiration rate, and patient movement; and a second monitor device configured to measure one or more physiological attributes associated with the patient, the second monitor device including one or more sensors contacting the patient; wherein, upon an alarm condition by the first monitor device, the second monitor device is configured to measure a physiological attribute and either: suppress the alarm condition when the second monitor device detects a non-alarm condition; or allow the alarm condition when the second monitor device detects an alarm condition.

In yet another aspect, a method for continuously monitoring a patient includes: measuring a first physiological attribute using a first monitor device, the first monitor device being a contactless device; detecting an alarm condition by the first monitor device; measuring a second physiological attribute using a second monitor device, the second monitor device including one or more sensors contacting the patient; and suppressing the alarm condition when the second monitor device detects a non-alarm condition.

DETAILED DESCRIPTION

The present disclosure relates to systems and methods for providing the continuous monitoring of patients.

Figure 1:
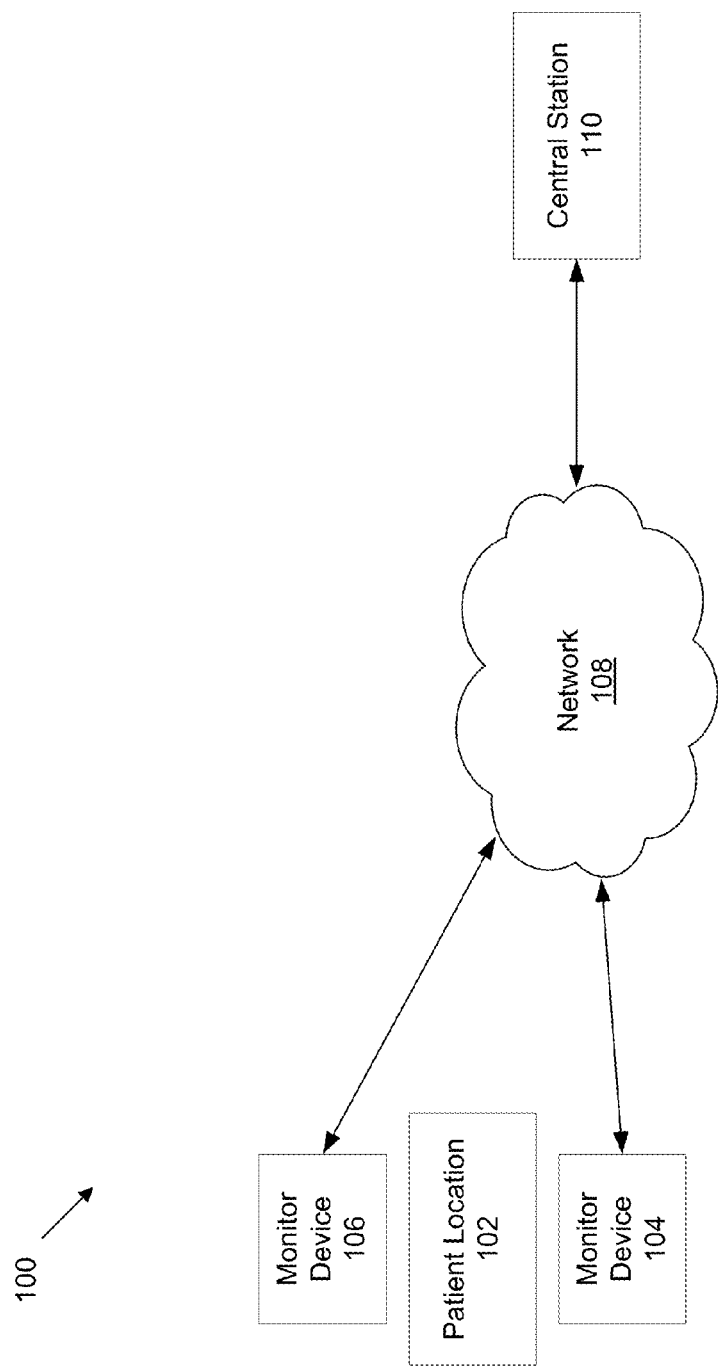
FIG. 1 shows an example system for continuous monitoring of a patient.

FIG. 1 is a block diagram illustrating an example system 100 for monitoring patients.

In this example, the patient is located at a patient location 102. The patient location 102 can be a hospital room or other location at which a patient is placed for monitoring. In this example, the patient location 102 is a patient bed in a hospital room or other caregiving location. In other examples, the patient location 102 can be a chair or other structure upon which a patient is rested. Finally, as described further below, the patient location 102 can include a space in which the patient resides, such as a hospital room.

In this example, the patient is being monitored by monitor devices 104, 106. The patient can, for example, be placed in the patient location 102 after surgery has been performed. The patient is monitored as the patient recovers from surgery. For example, if the patient was anesthetized during surgery, the patient is placed in patient location 102 after surgery and monitored as the patient wakes from the anesthesia.

The patient can be monitored at the patient location 102 for other reasons as well. For example, the patient can be ill or injured, and the monitor devices 104, 106 can be used to monitor the patient as the patient recovers.

For example, in some embodiments, the patient is monitored for events like fall situations. In such an example, the monitor devices 104, 106 are used to detect acute changes, such as the position of the patient (e.g., in or out of bed).

In yet other examples, the monitor devices 104, 106 are used to monitor the patient's level of ambulation. This is correlated with the vital signs for the patient. In such an embodiment, patient motion in and out of bed can be correlated with vital signs to determine a level of patient recovery. This can be used to determine when a patient is ready for discharge.

In yet other examples, the patient can wear one or both of the monitor devices 104, 106. In such an embodiment, the level of ambulation can be measured as the patient sleeps, sits, stands, and moves. Other configurations are possible.

In this example, the monitor device 104 is a device that monitors certain physiological attributes associated with the patient. The monitor device 104 is a contact-free patient monitor, meaning that the monitor device 104 does not directly contact the patient to measure the physiological attributes. Instead, the monitor device 104 uses piezoelectric technology to monitor such attributes as heart rate, respiration rate, and patient movement (e.g., if the patient is moving and/or if the patient has exited the patient location).

In this example, the monitor device 104 includes a sensor that is placed in proximity to the patient to measure the attributes. For example, the sensor of the monitor device 104 can be placed under a mattress of the patient's bed located at the patient location 102 or under a cushion of the patient's chair. The piezoelectric technology associated with the sensor allows the sensor to sense the specified attributes of the patient without directly contacting the patient.

In this example, the monitor device 104 is part of the EarlySense System manufactured by EarlySense of Waltham, Mass. Aspects of that system are described in U.S. patent application Ser. No. 11/552,872 filed on Oct. 25, 2006. Other devices can be used.

The monitor device 106 is a patient monitoring device that monitors various attributes associated with a patient, such as temperature, oxygen saturation level (SpO2), noninvasive blood pressure (NIBP), end tidal carbon dioxide (ETCO2), and respiration rate. In this example, the monitor device 106 is a contact device, in that the sensors of the monitor device 106 may contact the patient. For example, the NIBP sensor is a pressure cuff that is positioned around the patients arm to take measurements to estimate such attributes as the patient's blood pressure, movement, heart rate, etc.

In another example, the monitor device 106 includes a photoplethysmography sensor used to create a photoplethysmogram. Such a sensor can be used to create a high-accuracy and resolution heart rate measurements. Other sensors can be used.

In this example, the monitor device 106 is a Welch Allyn 1500 Patient Monitor manufactured by Welch Allyn of Skaneateles Falls, N.Y. Other devices can be used.

The monitor devices 104, 106 communicate with a network 108. In one example, the monitor devices 104, 106 and the network 108 are part of a CONNEX™ system from Welch Allyn of Skaneateles Falls, N.Y., although other systems can be used. In such an example, the monitor devices communicate through known protocols, such as the Welch Allyn Communications Protocol (WACP). WACP uses a taxonomy as a mechanism to define information and messaging. Taxonomy can be defined as description, identification, and classification of a semantic model. Taxonomy as applied to a classification scheme may be extensible. Semantic class-based modeling utilizing taxonomy can minimize the complexity of data description management by limiting, categorizing, and logically grouping information management and operational functions into families that contain both static and dynamic elements.

The network 108 is an electronic communication network that facilitates communication between the monitor devices 104, 106. An electronic communication network is a set of computing devices and links between the computing devices. The computing devices in the network use the links to enable communication among the computing devices in the network. The network 108 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices.

In various embodiments, the network 108 includes various types of links. For example, the network 108 can include wired and/or wireless links. Furthermore, in various embodiments, the network 108 is implemented at various scales. For example, the network 108 can be implemented as one or more local area networks (LANs), metropolitan area networks, subnets, wide area networks (such as the Internet), or can be implemented at another scale.

The monitor devices 104, 106 communicate through the network 108 with a central station 110. The central station 110 is a location at which a caregiver (e.g., a nurse or doctor) can monitor a plurality of patients. For example, the monitor devices 104, 106 send patient data to the central station 110, and the caregiver monitors the patient information at the central station 110.

In this example, the central station is a Welch Allyn Acuity® Central Monitoring Station manufactured by Welch Allyn. Other configurations are possible.

The monitor devices 104, 106 also provide alarming information to the central station 110. For example, if the monitor device 104 detects a lack of heart rate, respiration rate, and/or patient movement for a specified period of time, the monitor device 104 can communicate an alarm condition to the central station 110. This alerts a caregiver at the central station 110 of a condition that may require attention by the caregiver. Likewise, the monitor device 106 provides an alarm condition about abnormal attributes, such as a low pulse or respiration rate, to the central station 110.

However, in some instances, the alarm information is indicative of a false positive. For example, because the monitor device 104 is contactless, it is possible for the monitor device 104 to take a period of time to acquire the signal from the patient. Further, patient movement (e.g., rolling over, etc.) can cause loss of the signal. This slow acquisition time and loss of signal can result in alarm conditions that are false positives.

For example, the patient could roll over, and the monitor device 104 could lose the acquisition of the signal associated with the patient's heart rate. If the signal is not reacquired in a certain amount of time, the monitor device 104 may provide an alarm condition to the central station 110. This false positive may require a caregiver to check on the patient, wasting resources.

Likewise, the monitor device 106 can provide false positives. For example, if the SpO2 sensor becomes dislodged from the patient, the monitor device 106 loses the oxygen saturation levels for the patient, which could cause an alarm condition to be sent.

To minimize false positive information from being provided to the caregiver, a series of checks are provided between the monitor devices 104, 106. Generally, if one device indicates an alarm condition, information from the second device is checked prior to providing the alarm condition to the caregiver.

Figure 2:
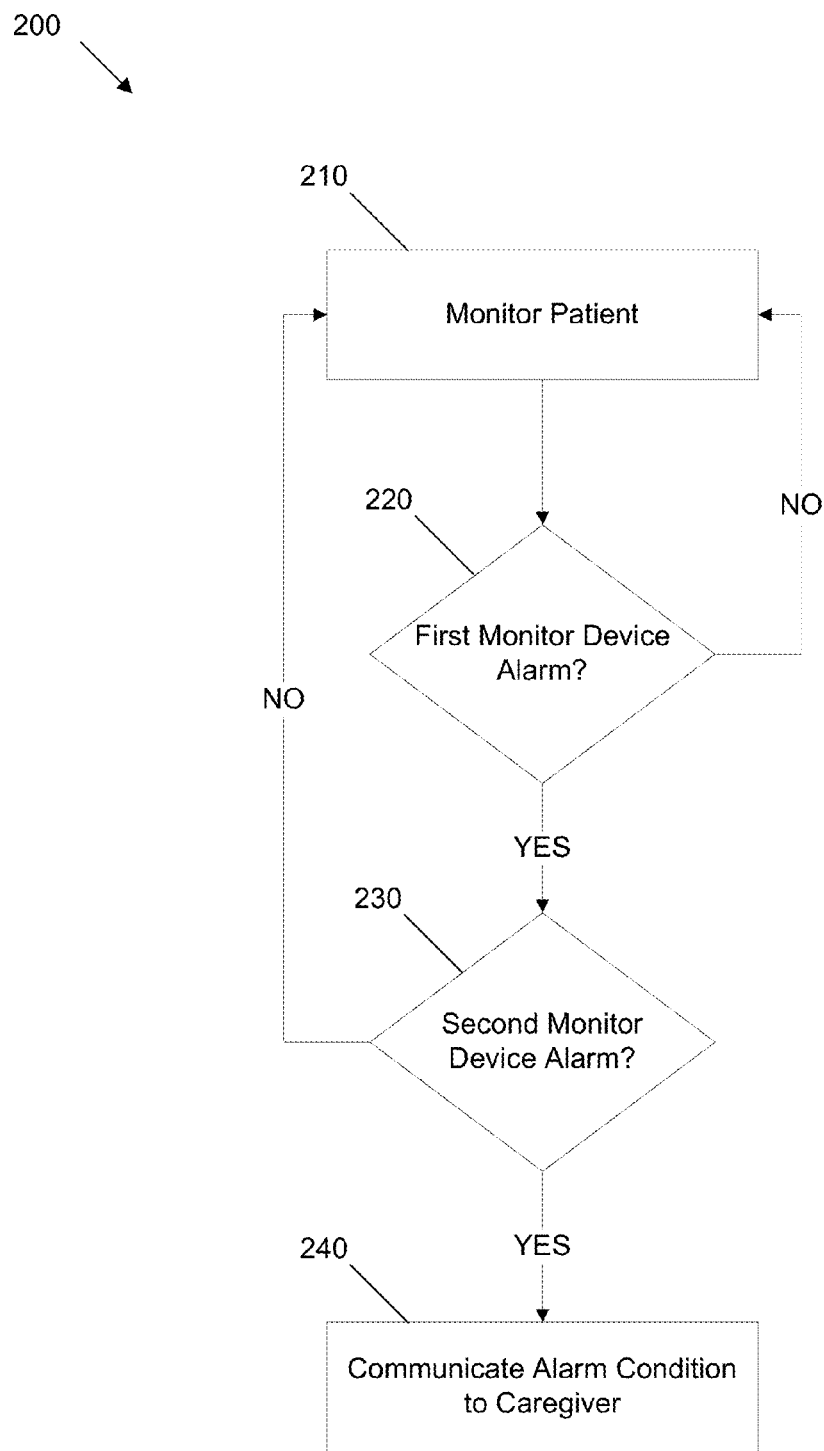
FIG. 2 shows an example method for continuous monitoring of a patient.

For example, referring now to FIG. 2, an example method 200 for the continuous monitoring of a patient is provided. In this example, the patient is monitored at operation 210 using, for example, the monitor devices 104, 106.

Next, at operation 220, a determination is made regarding whether or not one of the monitor devices (e.g., monitor device 104) is providing an indication of an alarm condition. If not, control is passed back to operation 210, and monitoring is continued.

If the monitor device is indicating an alarm condition, control is instead passed to operation 230, and a determination is made regarding whether or not the other of the monitor devices (e.g., monitor device 106) is providing an indication of an alarm condition. If not, control is passed back to operation 210, and continuous monitoring is continued.

If the monitor device is indicating an alarm condition, control is passed to operation 240, and the alarm condition is communicated to the caregiver. For example, the alarm condition can be sent to the central station.

The method 200 allows each of the two monitor devices 104, 106 to become a check and balance on the other of the monitor devices 104, 106, to minimize false alarming. In such a scenario, the method 200 utilizes the following logic.

| Monitor Device 104 | Monitor Device 106 | Alarm? |
| --- | --- | --- |
| Yes | Yes | Yes |
| No | Yes | No |
| Yes | No | No |
| No | No | No |

In one example, the monitor device 106 is used to minimize the false positives provided by the monitor device 104. For example, if the monitor device 104 loses the heart rate or respiration signals (e.g., when the patient moves) and starts to alarm, the monitor device 106 is consulted before the alarm condition is communicated to the caregiver at the central station 110.

In one embodiment, the monitor device 106 performs one or more measurements or actions to determine if alarming should occur upon receiving an alarm signal from the monitor device 104. The measurement can include taking a vital signs measurement (e.g., blood pressure, respiration rate, heart rate, oxygen saturation, or a combination thereof).

Figure 3:
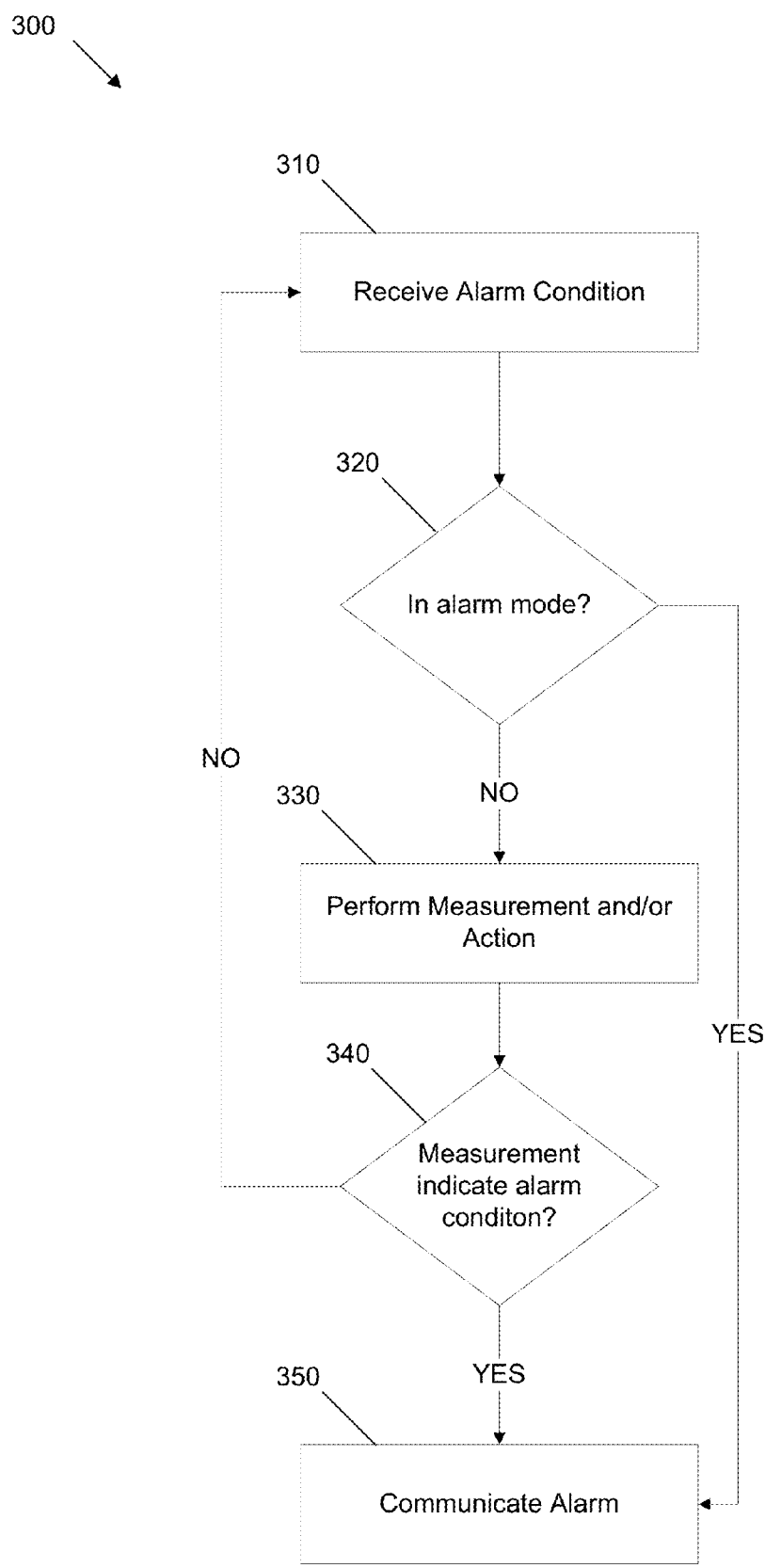
FIG. 3 shows an example method for confirming an alarm condition during continuous monitoring of a patient.

For example, referring now to FIG. 3, a method 300 for confirming an alarm condition during continuous monitoring of a patient is shown. At operation 310, the monitor device 106 receives an alarm condition from the monitor device 104. Next, at operation 320, a determination is made regarding whether or not the monitor device 106 is already indicating an alarm. If so, the alarm is communicated to the central station 110.

Alternatively, if the monitor device 106 is not already alarming, control is passed to operation 330, and the monitor device 106 performs one or more measurements and/or actions to determine if alarming is appropriate. This is done to minimize false alarming.

At operation 340, a determination is made regarding whether or not an alarm condition exists. If the measurement is indicative of an alarm condition, control is passed to operation 350, and the alarm is communicated. If not, control is passed back to operation 310, and the false positive is suppressed before the condition is used to alert the caregiver.

The alarming threshold for the system can be configurable. For example, the sensitivity for the system can be configured based upon different parameters, such as being dependent on the medication and/or surgical situation for the patient. In these examples, the system can be set to be more sensitive, which may result in greater false positives but a closer level of supervision. The converse is true if the sensitivity is decreased.

For example, the monitor device 106 can inflate the NIBP cuff to a sub-measurement pressure (e.g., 30 mmHg through 300 mmHg). At this pressure, the NIBP cuff can register patient movement in the form of physical movement, breathing, and/or heart rate. This information can be used to make a determination of whether or not alarming is appropriate. For example, if the NIBP cuff is expanded and movement is detected, the alarm condition for the monitor device 106 is set to non-alarm, and the alarm condition from the monitor device 104 can be suppressed. Conversely, if no movement is detected, the alarm condition can be communicated to the caregiver.

Figure 4:
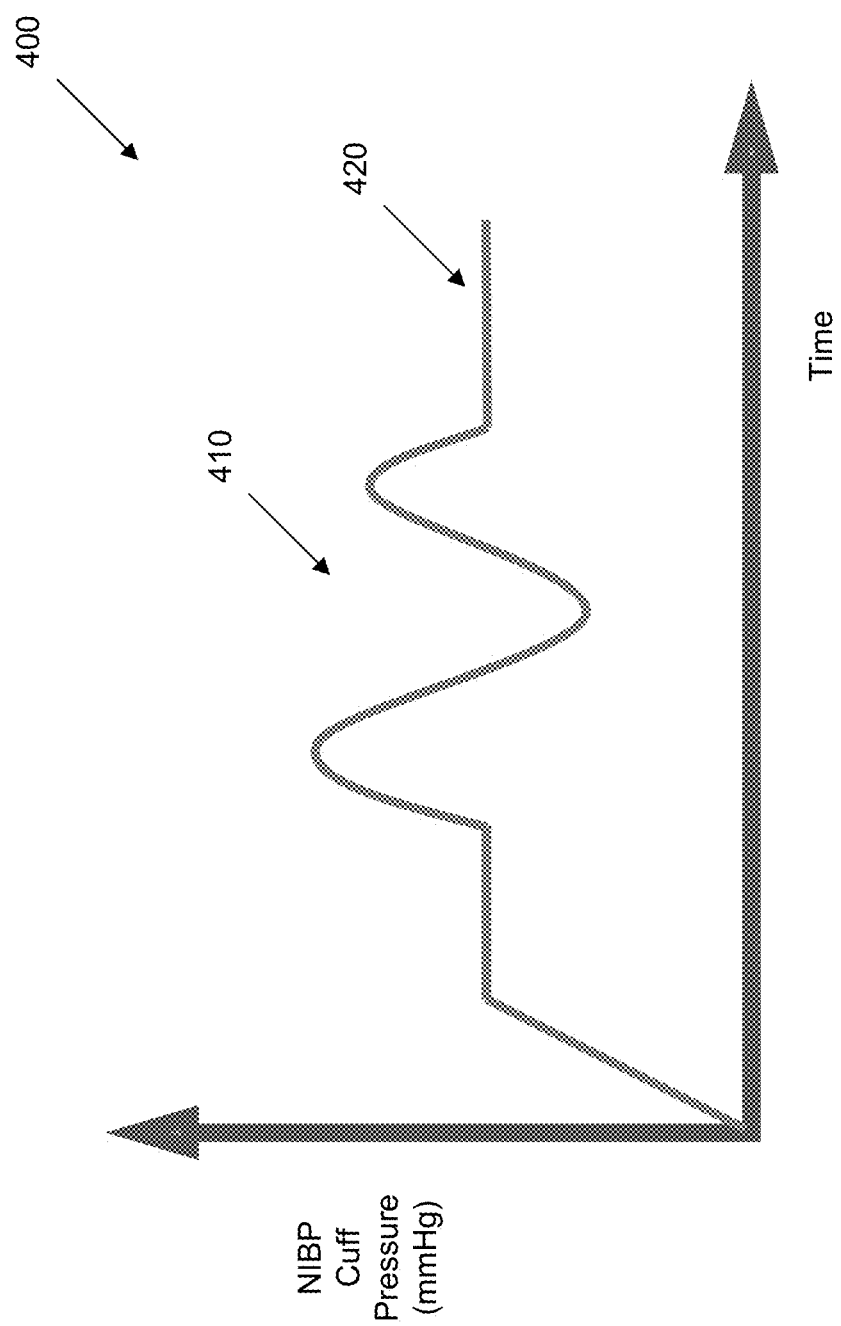
FIG. 4 shows an example chart with blood pressure data indicative of movement of the patient.

For example, FIG. 4 illustrates a chart 400 with data from a NIBP cuff that is plotted over time. The movement of the patient is manifested by the peaks and valleys shown at section 410. If the data is relative flat, such as at 420, the data would instead be indicative of no movement.

In another example, the SpO2 sensor of the monitor device 106 is used to determine whether an alarm condition exists. In this example, the SpO2 data is examined to look for indications of movement (e.g., spiking of the data) and/or heart rate (periodic). This information can be used to determine whether to suppress or allow the alarm condition to be communicated to the caregiver.

In some examples, the suppression of the alarm condition is time-based. For example, if the monitor device 104 alarms and the monitor device 106 senses movement, the monitor device 106 only suppresses the alarm transmission to the caregiver for a certain period of time. If that period of time expires and the monitor device 104 continues to alarm, the alarm condition is transmitted to the caregiver even if the monitor device 106 continues to sense an attribute that would allow for suppression of the alarm condition (e.g., movement).

In some examples, other factors can also be determined other than alarming conditions. For example, in another embodiment, the data from the devices is windowed or trended to determine a state of recovery for the patient—e.g., if a patient is starting to ambulate or worsen. These trends can be used to estimate a patient's progress, determine necessary interventions, and determine a proper discharge date.

The monitor devices 104, 106 and the central station 110 are computing devices. A computing device is a physical, tangible device that processes data. Example types of computing devices include personal computers, standalone server computers, blade server computers, mainframe computers, handheld computers, smart phones, special purpose computing devices, and other types of devices that process data.

Computing devices can include at least one central processing unit ("CPU"), a system memory, and a system bus that couples the system memory to the CPU. The system memory includes a random access memory ("RAM") and a read-only memory ("ROM"). A basic input/output system containing the basic routines that help to transfer information between elements within the device, such as during startup, is stored in the ROM. The device further includes a mass storage device. The mass storage device is able to store software instructions and data.

The mass storage device and its associated computer-readable data storage media provide non-volatile, non-transitory storage for the device. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the device can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the device.

The computing device can also include an input/output controller for receiving and processing input from a number of other devices, including a keyboard, a mouse, a touch user interface display screen, or another type of input device. Similarly, the input/output controller provides output to a touch user interface display screen, a printer, or other type of output device.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A system for providing continuous monitoring of a patient, the system comprising:
   a first monitor device configured to measure one or more physiological attributes associated with the patient, the first monitor device being a contactless device; and
   a second monitor device configured to measure one or more physiological attributes associated with the patient, the second monitor device including one or more sensors contacting the patient;
   wherein, upon an alarm condition indicating an abnormality by the first monitor device, the second monitor device is configured to measure a physiological attribute and suppress the alarm condition when the second monitor device detects a non-alarm condition; and
   wherein the second monitor device allows the alarm condition when the second monitor device detects an alarm condition.

2. The system of claim 1, wherein the first monitor device includes a piezoelectric device.

3. The system of claim 2, wherein the piezoelectric device is positioned under a mattress or cushion of a structure upon which the patient is laid.

4. The system of claim 3, wherein the piezoelectric device detects the patient's heart rate, respiration rate, and patient movement.

5. The system of claim 1, wherein the second monitor device inflates a blood pressure cuff to estimate movement of the patient.

6. The system of claim 5, wherein the blood pressure cuff is inflated to a sub-measurement pressure.

7. The system of claim 1, wherein suppression of the alarm condition by the second monitor device is limited to a specified time period.

8. The system of claim 7, wherein the second monitor device allows the alarm condition to be transmitted when the specified time period expires and the first monitor device continues to issue the alarm condition.

9. A system for providing continuous monitoring of a patient, the system comprising:
   a first monitor device configured to measure one or more physiological attributes associated with the patient, the first monitor device being a piezoelectric device that measures the physiological attributes without contact, and wherein the physiological attributes including heart rate, respiration rate, and patient movement; and
   a second monitor device configured to measure one or more physiological attributes associated with the patient, the second monitor device including one or more sensors contacting the patient;
   wherein, upon an alarm condition indicating an abnormality by the first monitor device, the second monitor device is configured to measure a physiological attribute and either:
      (i) suppress the alarm condition when the second monitor device detects a non-alarm condition; or
      (ii) allow the alarm condition when the second monitor device detects an alarm condition; and
   wherein the second monitor device inflates a blood pressure cuff to a sub-measurement pressure to estimate movement of the patient and detects the non-alarm condition when movement of the patient is detected.

10. The system of claim 9, wherein the piezoelectric device is positioned under a mattress of a bed upon which the patient is laid.

11. The system of claim 9, wherein suppression of the alarm condition by the second monitor device is limited to a specified time period.

12. The system of claim 11, wherein the second monitor device allows the alarm condition to be transmitted when the specified time period expires and the first monitor device continues to issue the alarm condition.

13. A method for continuously monitoring a patient, the method comprising:
   measuring a first physiological attribute using a first monitor device, the first monitor device being a contactless device;
   detecting an alarm condition indicating an abnormality by the first monitor device;
   measuring a second physiological attribute using a second monitor device, the second monitor device including one or more sensors contacting the patient, and the measuring including:
      inflating a blood pressure cuff;
      estimating movement of the patient based upon a pressure characteristic as measured by the blood pressure cuff, the pressure characteristic including a pressure increase or decrease indicative of movement; and
      determining a non-alarm condition when movement of the patient is detected;
   suppressing the alarm condition when the second monitor device detects the non-alarm condition; and
   transmitting the alarm condition when the second monitor device detects an alarm condition.

14. The method of claim 13, wherein the first monitor device includes a piezoelectric device.

15. The method of claim 14, further comprising positioning the piezoelectric device under a mattress of a bed upon which the patient is laid.

16. The method of claim 13, further comprising trending data from the first and second monitor devices to determine a state of recovery for the patient.

* * * * *